US00PP10074P

United States Patent [19]

Challet

[11] Patent Number: Plant 10,074

[45] Date of Patent: Oct. 21, 1997

[54] CHRYSANTHEMUM PLANT NAMED 'CHAGIRA'

[75] Inventor: Jean Pierre Challet, Nuaille, France

[73] Assignee: Selection New Plant Sarl, Le Luc, France

[21] Appl. No.: 772,913

[22] Filed: Dec. 24, 1996

[51] Int. Cl.[6] ..... A01H 5/00

[52] U.S. Cl. ..... Plt./74.1

[58] Field of Search ..... Plt./74.1, 82.4, Plt./82.5

*Primary Examiner*—Howard J. Locker

*Attorney, Agent, or Firm*—Burns, Doane, Swecker & Mathis, L.L.P.

[57] ABSTRACT

A new and distinct Chrysanthemum cultivar named 'Chagira' is provided. The new cultivar was the result of a controlled breeding program. Attractive small light pink daisy blossoms having a yellow center are formed in profusion as a round ball which surrounds the plant. Flower production is carried out on a natural production cycle. The plant possesses strong stems, forms attractive leaves, and commonly assumes a height of approximately 25 to 30 cm. The blossom coloration contrasts nicely with the dark green foliage. The new cultivar is particularly well suited for use in the production of a decorative pot Chrysanthemum. No growth regulator is necessary to achieve the very short plant height.

1 Drawing Sheet

SUMMARY OF THE INVENTION

The present invention comprises a new and distinct cultivar of Chrysanthemum, botanically known as *Dendranthema grandiflora*, and hereinafter is referred to by the cultivar name 'Chagira'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during November 1986 at Nuaille, Trementines, France. The female parent (i.e., the seed parent) was the '8327-2' cultivar (non-patented in the United States and never even offered for sale in France) having yellow flower, generally poor foliage, and a tall plant height, and the male parent (i.e., the pollen parent) was the '8471-9' cultivar (non-patented in the United States and never even offered for sale in France) having a very short and bushy growth habit. The parentage of the new cultivar can be summarized as follows:

'8327-2'×'8471-9'.

The seeds resulting from the above pollination were sown and many small plantlets were obtained which were physically biologically different from each other. Selective study resulted in the identification of a single plant of the new cultivar.

It was found that the new cultivar of the present invention:

(a) exhibits in profusion attractive small pink daisy blossoms having a yellow center,
(b) is highly amenable to branching by pinching,
(c) forms attractive foliage,
(d) achieves a very short plant height, and
(e) is particularly well suited for pot mum production on a natural production cycle.

The new cultivar is intended primarily as a decorative pot Chrysanthemum for growing outdoors at temperatures above freezing. However, the new cultivar also can be grown indoors.

In the absence of debudding the new cultivar commonly forms approximately 7 to 9 blossoms per stem. Also, the new cultivar can be grown as a disbud to form striking blooms. An increased number of branches readily can be induced by pinching. The pinching of a cutting commonly produces approximately 10 to 12 stems per cutting. No growth regulator is required to produce the very short plant height; however, a growth regulator optionally can be utilized.

The new cultivar can be considered to be an October-flowering greenhouse variety with the natural flowering season commonly occurring in weeks 42 to 43 of the year. The blossoms are long lasting and commonly can be maintained on the plant for approximately two weeks.

Asexual reproduction of the new cultivar by cuttings initially taken during 1987, as performed in Nuaille, Trementines, France, in a controlled environment has demonstrated that the characteristics of the new cultivar as herein described are firmly fixed and are retained through successive generations of asexual propagation.

'Chagira' has not been observed under all possible environmental conditions to date. Accordingly, it is possible that the phenotype may vary somewhat with variations in the environment, such as temperature, light, day length, contact with pesticides and/or subjection to growth retardant treatments.

The new 'Chagira' cultivar is being marketed under the SUPRA trademark.

BRIEF DESCRIPTION OF THE PHOTOGRAPH

The accompanying photograph was prepared during March, 1996, and shows as nearly true as it is reasonably possible to make the same in a color illustration of this character, typical plants and plant parts of the new cultivar of the present invention. The plants were 12 weeks of age and were grown at Nuaille, Trementines, France, under standard greenhouse conditions which approximate those commonly utilized for the production of decorative pot mums. The plants had been pinched once and had not been disbudded. No growth regulator was utilized.

DETAILED DESCRIPTION

Figures 1, 2, 3, 4, 5, 6, 7, 8, 9, 10, 11, 12, 13, 14:
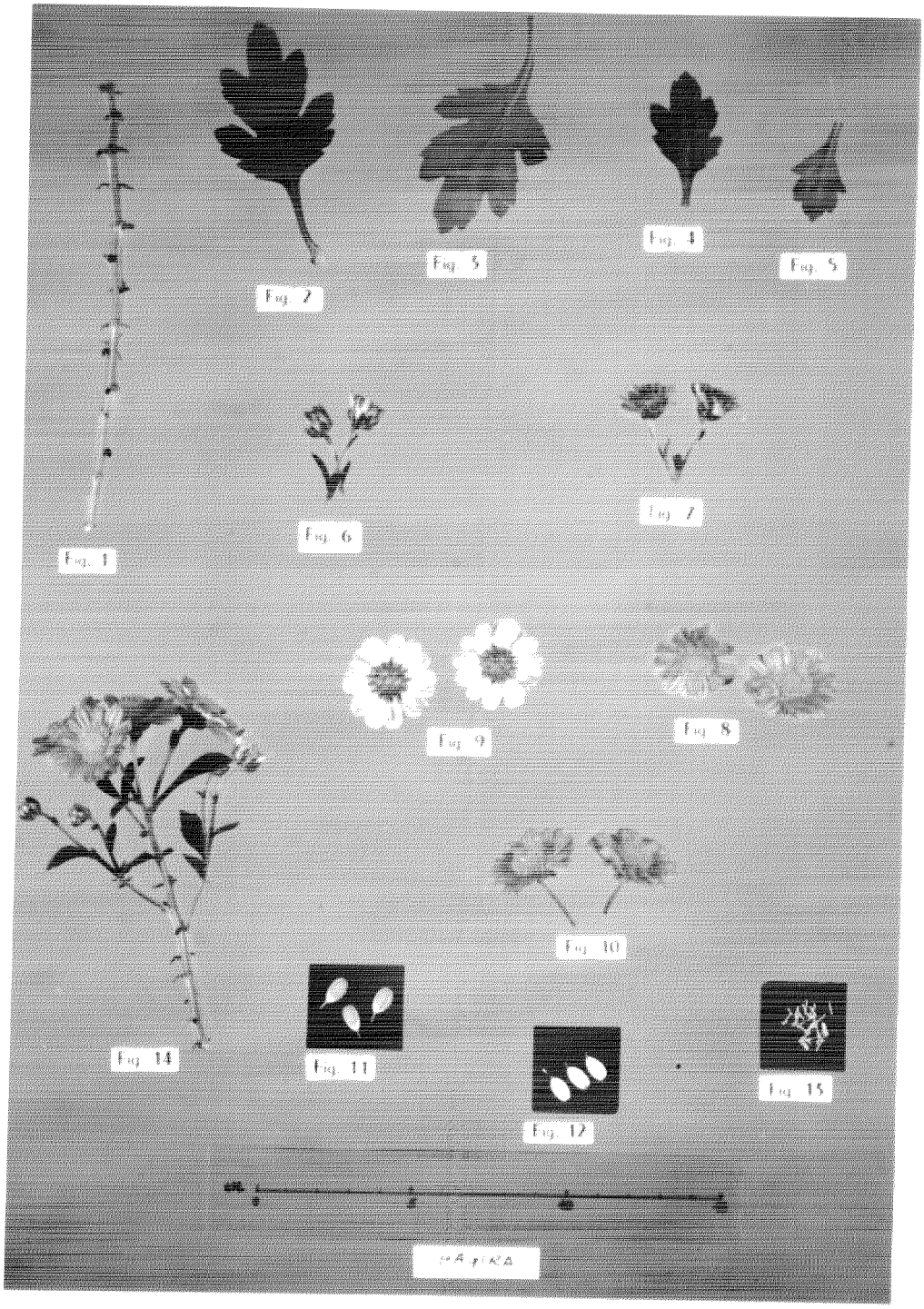
FIG. 1 illustrates a typical stem.
FIG. 2 illustrates the top view of a typical leaf from the lower part of the stem.
FIG. 3 illustrates the under view of a typical leaf from the lower part of the stem.
FIG. 4 illustrates the top view of a typical leaf from the upper part of the stem.
FIG. 5 illustrates the under view of a typical leaf from the upper part of the stem.
FIG. 6 illustrates the side view of a pair of largely unopened buds.
FIG. 7 illustrates the side view of a pair of typical flowers in the course of opening.
FIG. 8 illustrates the top view of a pair of typical opened flowers.
FIG. 9 illustrates the under view of a pair of typical opened flowers.
FIG. 10 illustrates the side view of a pair of typical opened flowers.
FIG. 11 illustrates the top view of three typical outer-ray florets.
FIG. 12 illustrates an under view of three typical outer-ray florets.
FIG. 13 illustrates an array of typical disc florets.
FIG. 14 illustrates a side of a typical inflorescence wherein the flowers are in various stages of opening.

The chart used in the identification of colors described hereafter is the R.H.S. Colour Chart of The Royal Horticultural Society, London, England. In some instances more common color terms are provided and are to be accorded their usual dictionary significance. The plants described were grown at Nuaille, Trementines, France, in 20 cm. pots, three plants to a pot, and were rooted in late May and stopped in early July. All primary laterals were retained. The plants were grown outdoors until late September and then in the greenhouse with a minimum temperature of 15.5° C. These conditions approximate those commonly utilized for the production of decorative pot mums.

Classification:

*Botanical.*—*Dendranthema grandiflora*, cv. 'Chagira'.

*Commercial.*—Decorative pot mum.

Inflorescence

A. Capitulum:

*Type.*—Daisy-eyed.

*Number of rows of involucral bracts.*—Generally five or less.

*Diameter across face.*—Approximately 25 to 35 mm. on average when fully expanded.

*Frequency.*—Corymbiform.

*Outside bud coloration.*—Greyed-Purple Group 186B.

B. Corolla of ray and disc florets:

*Receptacle.*—Small and conical flat.

*Disc florets.*—Tubular, yellow, short to medium in overall length, numerous, massed, and generally clearly visible at all stages of flower head development.

*General tonality.*—Yellow towards the center.

*Color of disc florets.*—Before dehiscence, greenish-yellow, and at anther dehiscence, yellow towards the center.

*Color ray florets.*—Outer side: At maturity White Group 155D but whiter and brighter, and lightly tinged with Red-Purple Group 70A. Inner side: At maturity between Red-Purple Group 70A and Red-Purple Group 70B becoming slightly paler towards the tip.

*Configuration ray florets.*—The longitudinal axis of the majority of the ray florets is reflected very weakly towards the tip, and the strength of the curvature is variable. However, the longitudinal axis of the ray florets of the outer rows generally is straight. The length of the corolla tube of the ray florets is short. The cross-section of the ray florets is convex, there is no keel, and the ray florets tend to be strongly ribbed. The ray florets generally are thin but occasionally are somewhat thicker, and their surfaces are textured. The tips of the ray florets are rounded, and they sometimes are dentate. The ray florets are approximately 1 cm. in length on average and approximately 0.7 cm. in width on average.

C. Reproductive organs:

*Androecium.*—Generally present with disc florets and absent in ray florets.

*Gynoecium.*—Generally present with most disc florets and with most ray florets.

*Pollen.*—Generally formed in only a slight quantity and golden-yellow in coloration.

*Fragrance.*—Typical of Chrysanthemum.

Plant

A. General appearance:

*Height.*—Very short, and approximately 25 to 30 cm. in height on average.

B. Foliage:

*Color.*—Green Group 137A.

*Configuration.*—Lobed (as illustrated).

*Texture.*—Fleshy.

*Serration.*—Fine to medium.

*Length of lower lobe.*—Medium to long, and occasionally only medium.

*Shape of base of sinus.*—Rounded.

*Shape of base of leaf.*—Rounded.

*Claw in base sinus between lateral lobes.*—Absent.

*Margins of sinus between lateral lobes.*—Converging, and occasionally diverging.

*Apex.*—Mucronate.

*Stems.*—Thin, angular in cross section, with some brittleness, near Yellow-Green Group 144A (as illustrated) in coloration, and with somewhat uniform anthocyanin coloration along the stem.

I claim:

1. A new and distinct cultivar of Chrysanthemum plant named 'Chagira', substantially as herein shown and described, which:

(a) exhibits in profusion attractive small pink daisy blossoms having a yellow center,
(b) is highly amenable to branching by pinching,
(c) forms attractive foliage,
(d) achieves a very short plant height, and
(e) is particularly well suited for pot mum production on a natural production cycle.

* * * * *